(12) United States Patent
Xu et al.

(10) Patent No.: US 7,173,699 B2
(45) Date of Patent: *Feb. 6, 2007

(54) SPECTROSCOPIC SCATTEROMETER SYSTEM

(75) Inventors: Yiping Xu, Cupertino, CA (US); Ibrahim Abdulhalim, Kfar Manda (IL)

(73) Assignee: KLA-Tencor Technologies Corporation, Milpitas, CA (US)

( * ) Notice: Subject to any disclaimer, the term of this patent is extended or adjusted under 35 U.S.C. 154(b) by 276 days.

This patent is subject to a terminal disclaimer.

(21) Appl. No.: 10/251,246

(22) Filed: Sep. 20, 2002

(65) Prior Publication Data

US 2003/0058443 A1 Mar. 27, 2003

Related U.S. Application Data

(63) Continuation of application No. 09/036,557, filed on Mar. 6, 1998, now Pat. No. 6,483,580.

(51) Int. Cl.
*G01J 4/00* (2006.01)
(52) U.S. Cl. .................................................. 356/369
(58) Field of Classification Search ........ 356/364–369, 356/319, 328, 73, 630, 300, 446–448, 326, 356/445
See application file for complete search history.

(56) References Cited

U.S. PATENT DOCUMENTS

| 4,039,370 A | 8/1977 | Kleinknecht |
| 4,141,780 A | 2/1979 | Kleinknecht et al. |
| 4,200,396 A | 4/1980 | Kleinknecht et al. |
| 4,303,341 A | 12/1981 | Kleinknecht et al. |
| 4,330,213 A | 5/1982 | Kleinknecht et al. |
| 4,408,884 A | 10/1983 | Kleinknecht et al. |
| 4,668,860 A | 5/1987 | Anthon |
| 4,672,196 A | 6/1987 | Canino |
| 4,695,162 A | 9/1987 | Itonaga et al. |
| 4,710,642 A | 12/1987 | McNeil |
| 4,790,659 A | 12/1988 | Erman et al. |

(Continued)

FOREIGN PATENT DOCUMENTS

EP 0480620 A2 4/1992

(Continued)

OTHER PUBLICATIONS

"Ultraviolet-visible ellipsometry for process control during the etching of submicrometer features," N. Blayo et al., *J. Opt. Soc. Am. A*, vol. 12, No. 3, Mar. 1995, pp. 591-599.

(Continued)

*Primary Examiner*—Tu T. Nguyen
(74) *Attorney, Agent, or Firm*—Parsons Hsue & de Runtz LLP (57) ABSTRACT

Before the diffraction from a diffracting structure on a semiconductor wafer is measured, where necessary, the film thickness and index of refraction of the films underneath the structure are first measured using spectroscopic reflectometry or spectroscopic ellipsometry. A rigorous model is then used to calculate intensity or ellipsometric signatures of the diffracting structure. The diffracting structure is then measured using a spectroscopic scatterometer using polarized and broadband radiation to obtain an intensity or ellipsometric signature of the diffracting structure. Such signature is then matched with the signatures in the database to determine the grating shape parameters of the structure.

112 Claims, 5 Drawing Sheets

U.S. PATENT DOCUMENTS

| | | | |
|---|---|---|---|
| 4,905,170 A | 2/1990 | Forouhi et al. | |
| 4,991,971 A | 2/1991 | Geary et al. | |
| 4,999,014 A | 3/1991 | Gold et al. | |
| 5,032,734 A | 7/1991 | Orazio, Jr. et al. | |
| 5,042,951 A | 8/1991 | Gold et al. | |
| 5,076,696 A | 12/1991 | Cohn et al. | |
| 5,164,790 A | 11/1992 | McNeil et al. | |
| 5,166,752 A | 11/1992 | Spanier et al. | |
| 5,241,369 A | 8/1993 | McNeil et al. | |
| 5,329,357 A | 7/1994 | Bernoux et al. | |
| 5,333,052 A | 7/1994 | Finarov | |
| 5,337,146 A * | 8/1994 | Azzam | 356/367 |
| 5,365,340 A | 11/1994 | Ledger | |
| 5,381,233 A | 1/1995 | Chao et al. | |
| 5,408,322 A * | 4/1995 | Hsu et al. | 356/369 |
| 5,412,473 A | 5/1995 | Rosencwaig et al. | |
| 5,416,594 A | 5/1995 | Gross et al. | |
| 5,420,680 A | 5/1995 | Isobe et al. | |
| 5,494,697 A | 2/1996 | Blayo et al. | |
| 5,503,707 A | 4/1996 | Maung et al. | |
| 5,504,582 A | 4/1996 | Johs et al. | |
| 5,521,706 A | 5/1996 | Green et al. | |
| 5,526,117 A | 6/1996 | Wielsch et al. | |
| 5,596,411 A | 1/1997 | Fanton et al. | |
| 5,604,581 A | 2/1997 | Liu et al. | |
| 5,607,800 A * | 3/1997 | Ziger | 430/8 |
| 5,608,526 A | 3/1997 | Piwonka-Corle et al. | |
| 5,610,392 A | 3/1997 | Nagayama et al. | |
| 5,625,455 A | 4/1997 | Nash et al. | |
| 5,631,171 A | 5/1997 | Sandstrom et al. | |
| 5,638,178 A | 6/1997 | Lacey et al. | |
| 5,666,201 A | 9/1997 | Johs et al. | |
| 5,739,909 A | 4/1998 | Blayo et al. | |
| 5,757,671 A | 5/1998 | Drevillon et al. | |
| 5,805,290 A | 9/1998 | Ausschnitt et al. | |
| 5,825,498 A | 10/1998 | Thakur et al. | |
| 5,835,221 A | 11/1998 | Lee et al. | |
| 5,867,276 A * | 2/1999 | McNeil et al. | 356/445 |
| 5,880,838 A * | 3/1999 | Marx et al. | 356/498 |
| 5,923,423 A | 7/1999 | Sawatari et al. | |
| 5,956,148 A | 9/1999 | Celii | |
| 5,963,329 A * | 10/1999 | Conrad et al. | 356/613 |
| 6,031,615 A | 2/2000 | Meeks et al. | |
| 6,100,985 A | 8/2000 | Scheiner et al. | |
| 6,104,486 A * | 8/2000 | Arimoto | 356/300 |
| 6,118,525 A | 9/2000 | Fossey et al. | |
| 6,271,047 B1 | 8/2001 | Ushio et al. | |
| 6,278,519 B1 | 8/2001 | Rosencwaig et al. | |
| 6,323,946 B1 | 11/2001 | Norton | |
| 6,483,580 B1 | 11/2002 | Xu et al. | |
| 6,590,656 B2 | 7/2003 | Xu et al. | |
| 6,603,542 B1 | 8/2003 | Chase et al. | |
| 6,657,736 B1 | 12/2003 | Finarov et al. | |
| 6,829,057 B2 | 12/2004 | Opsal et al. | |

FOREIGN PATENT DOCUMENTS

| | | |
|---|---|---|
| EP | 0480620 A3 | 9/1992 |
| EP | 1124163 A2 | 8/2001 |
| EP | 1073876 B1 | 12/2004 |
| EP | 1508772 A1 | 2/2005 |
| EP | 1124163 A3 | 7/2005 |
| WO | WO 99/45340 | 9/1999 |
| WO | WO 00/35002 | 6/2000 |

OTHER PUBLICATIONS

International Preliminary Examination Report mailed Jul. 3, 2000.
Written Opinion mailed Mar. 27, 2000.
"Optical dispersion relations for amorphous semiconductors and amorphous dielectrics," A.R. Forouhi et al., *Physical Review B*, vol. 34, No. 10, Nov. 15, 1986, pp. 7018-7026.

"Optical properties of crystalline semiconductors and dielectrics," A.R. Forouhi et al., *Physical Review B*, vol. 38, No. 3, Jul. 15, 1998, pp. 1865-1873.
"Optical characterization of amorphous and polycrystalline silicon films," E. Ibok et al., *Solid State Technology*, Aug. 1995.
"Convergence of the coupled-wave method for metallic lamellar diffraction gratings," L. Li et al., *Journal of the Optical Society of America A*, vol. 10, No. 6, Jun. 1993, pp. 1184-1188.
"Multilayer modal method for diffraction gratings of arbitrary profile, depth, and permitivity," L. Li, *Journal of the Optical Society of America A*, vol. 10, No. 12, Dec. 1993, pp. 2581-2591.
"A model analysis of lamelar diffraction gratings in a conical mounting," L. Li, *Journal of Modern Optics*, vol. 40, No. 4, 1993, pp. 553-573.
"Metrology of subwavelength photoresist gratings using optical scatterometry," C.J. Raymond et al., *J. Vac. Sci. Technol. B*, vol. 13, No. 4, Jul./Aug. 1995, pp. 1484-1495.
"Line size effects on ultraviolet reflectance spectra," D.H. Ziger et al., *Opt. Eng.*, vol. 36, No. 1, Jan. 1997, pp. 243-250.
"Scatterometry and the Simulation of Diffraction-Based Metrology," S. Sohail et al., *Microlithography World*, Jul./Aug./Sep. 1993, pp. 5-16.
"A broadband UV small spot spectroscopic ellipsometer," T.R. Corle, *SPIE Microlithography*, 1995, pp. 1-12.
"Rigorous coupled-wave analysis of planar-grating diffraction," M.G. Moharam et al., *J. Opt. Soc. Am.*, vol. 71, No. 7, Jul. 1981, pp. 881-818.
"Stable implementation of the rigorous coupled-wave analysis for surface-relief gratings: enhanced transmittance matrix approach," M.G. Moharam et al., *J. Opt. Soc. Am. A*, vol. 12, No. 5, May 1995, pp. 1077-1086.
"Analysis and Applications of Optical Diffraction by Gratings," T.K. Gaylord et al., *Proceedings of the IEEE*, vol. 73, No. 5, May 1985, pp. 894-937.
Mills. D. W. et al., "Spectral ellipsometry on patterned wafers", *SPIE's Microelectronic Manufacturing: Process, Equipment, and Materials Control in Integrated Circuit Manufacturing, SPIE vol. 2637, Austin (USA)*, 1995.
European Patent Office, "Communication of the European Search Report", mailed in related EP 04078145.2 on Dec. 28, 2004.
Arimoto, H., "Precise Line-and-Space Monitoring Results by Ellipsometry", *Jpn. J. Appl. Phys.* vol. 36, Part 2, No. 2A, pp. L173-L175 (Feb. 1997).
Diffraction: www.scienceworld.wolfram.com/physics/Diffraction.html, 2 pages, printed Jan. 27, 2004.
Li, L., "Formulation and Comparison of Two Recursive Matrix Algorithms for Modeling Layered Diffraction Gratings," *J. Opt. Soc. Am. A*, vol. 13, No. 5, pp. 1024-1035 (May 1996).
"Spectroscopic Ellipsometry—A Technology Primer", KLA-Tencor, 12 pages.
McNeil, J.R. et al., "Scatterometry Applied to Microelectronics Processing—Part 1", Solid State Technology, Mar. 1993, 3 pages.
McNeil, J.R. et al., "Scatterometry Applied to Microelectronics Processing—Part 2", Solid State Technology, Apr. 1993, pp. 53-56.
Moharam, M.G., "Coupled-Wave Analysis of Two-Dimensional Dielectric Gratings," Proc. SPIE, vol. 883, Holographics Optics: Design and Applications, pp. 8-11 (1988).
Moharam, M.G. et al., "Formulation for Stable and Efficient Implementation of the Rigorous Coupled-Wave Analysis of Binary Gratings," J. Opt. Soc. Am. A, vol. 12, pp. 1068-1076 (May 1995).
Physics 204 Laboratory 13 Diffraction Grating, www.physics.fsu.edu/courses/fall98/phy2049c/labs/L13.pdf, 7 pages.
Coulombe et al., "Ellipsometric-Scatterometry for sub-0.1 μm CD Measurements", Center for High Technology Materials, Univeristy of New Mexico, SPIE vol. 3332, pp. 283-292 (1998).
Murnane et al., "Developed Photoresist Metrology Using Scatterometry", Center for High Technology Materials, University of New Mexico, SPIE vol. 2196, pp. 47-59 (Mar. 1994).
R. Pforr, et al., "In-Process Image Detecting Technique For Determination of Overlay, And Image Quality For ASM-L Wafer Stepper", *SPIE vol. 1674 Optical/Laser Microlithography V* (1992) pp. 594-608.

* cited by examiner

SPECTROSCOPIC SCATTEROMETER SYSTEM

CROSS REFERENCE TO RELATED APPLICATION

This application is a continuation of U.S. patent application Ser. No. 09/036,557, filed Mar. 6, 1998, now U.S. Pat. No. 6,483,580.

BACKGROUND OF THE INVENTION

This invention relates in general to scatterometers and in particular, to a spectroscopic scatterometer system.

As the integration and speed of microelectronic devices increase, circuit structures continue to shrink in dimension size and to improve in terms of profile edge sharpness. The state-of-the-art devices require a considerable number of process steps. It is becoming increasingly important to have an accurate measurement of submicron linewidth and quantitative description of the profile of the etched structures on a pattern wafer at each process step. Furthermore, there is a growing need for wafer process monitoring and close-loop control such as focus-exposure control in photolithography.

Diffraction-based analysis techniques such as scatterometry are especially well suited for microelectronics metrology applications because they are nondestructive, sufficiently accurate, repeatable, rapid, simple and inexpensive relative to critical dimension-scanning electron microscopy (CD-SEM).

Scatterometry is the angle-resolved measurement and characterization of light scattered from a structure. For structures that are periodic, incident light is scattered or diffracted into different orders. The angular location $\theta_r$ of the $m^{th}$ diffraction order with respect to the angle of incidence $\theta_i$ is specified by the grating equation:

$$\sin\theta_i + \sin\theta_r = m\frac{\lambda}{d} \quad (1)$$

where $\lambda$ is the wavelength of incident light and d the period of the diffracting structure.

The diffracted light pattern from a structure can be used as a "fingerprint" or "signature" for identifying the dimensions of the structure itself. In addition to period, more specific dimensions, such as width, step height, and the shape of the line, the thickness of the underlay film layers, and angle of the side-walls, referred to below as parameters of the structure, can also be measured by analyzing the scatter pattern.

Since the periods of the gratings in the state-of-the-art devices are generally below 1 μm, only the $0^{th}$ and $+/-1^{ST}$ diffraction orders exist over a practical angular range. A traditional scatterometer that measures the entire diffraction envelope does not provide the data required for an accurate analysis. One prior optical technique for characterizing submicron periodic topographic structures is called 2-Θ scatterometry.

The 2-Θ scatterometer monitors the intensity of a single diffraction order as a function of the angle of incidence of the illuminating light beam. The intensity variation of the $0^{th}$ as well as higher diffraction orders from the sample provides information which is useful for determining the properties of the sample which is illuminated. Because the properties of a sample are determined by the process used to fabricate the sample, the information is also useful as an indirect monitor of the process.

In 2-Θ scatterometry, a single wavelength coherent light beam, for example, a helium-neon laser, is incident upon a sample mounted on a stage. By either rotating the sample stage or illumination beam, the angle of incidence on the sample is changed. The intensity of the particular diffraction order (such as zeroth-order or first order) as a function of incident angle, which is called a 2-Θ plot or scatter "signature" is then downloaded to a computer. In order to determine the different parameters such as linewidth, step height, shape of the line, and angle of the side-walls (the angle the side-wall makes with the underlying surface, also known as the "wall angle"), a diffraction model is employed. Different grating parameters outlined above are parameterized and a parameter space is defined by allowing each grating-shaped parameter to vary over a certain range.

A rigorous diffraction model is used to calculate the theoretical diffracted light fingerprint from each grating in the parameter space, and a statistical prediction algorithm is trained on this theoretical calibration data. Subsequently, this prediction algorithm is used to determine the parameters that correspond to the 2-Θ plots or scatter "signature" measured from a target structure on a sample.

While 2-Θ scatterometry has been useful in some circumstances, it has many disadvantages. The periodic diffracting structure is frequently situated over one or more films that transmit light. Therefore, any diffraction model employed must account for the thicknesses and refractive indices of all films underneath the diffracting structure. In one approach, the thickness and refractive indices of all layers must be known in advance. This is undesirable since frequently, these quantities are not known in advance. In particular, the film thickness and optical indices of materials used in semiconductor fabrication often vary from process to process.

Another approach to solve the above problem is to include all unknown parameters in the model, including film thickness and optical indices of underlying film materials. By thus increasing the number of variables in the model, the number of signatures that has to be calculated increase exponentially, so that the computation time involved renders such approach inappropriate for real-time measurements.

Furthermore, since the intensity of the particular diffraction order as a function of incidence angle of the sampling beam is acquired sequentially as the incident angle is varied, data acquisition for the 2-Θ plot or scatter "signature" is slow and the detected intensity is subject to various noise sources such as system vibration and random electronic noise which may change over time as the incident angle is varied.

Another approach is proposed by Ziger in U.S. Pat. No. 5,607,800. In this approach, where the measurement of a particular patterned film is desired, a first patterned arrangement having predetermined and known grating characteristics close to those of the patterned film to be measured is first made, such as by forming a line-and-space pattern on a first wafer. A spectroreflectometer is then used to measure the amplitude of reflected signals from such first arrangement to obtain a signature. Then a second patterned arrangement having known grating characteristics close to those of the patterned film to be measured, such as another line-and-space pattern on a second wafer, is obtained and a spectroreflectometer is used to measure the amplitude of reflected signal from such arrangement to obtain a second signature. The process is repeated on additional wafers and the signatures so formed are organized as a database. Then, the target pattern film of the sample is measured using a spectroreflectometer and its signature compared to those present in the database. The signature in the database that matches the signature of the target film is then used to find the grating characteristics or parameters of the target film.

Ziger's approach is limited and impractical, since it requires replication of multiple reference patterns analogous to the target pattern and measurements of such reference patterns to construct a database before a measurement can be made of the target pattern. Ziger's approach also requires contrast difference between the reflectivity of the film versus the reflectivity of the substrate. In other words, Ziger's method cannot be used to measure the grating characteristics on line patterns made of a material having a reflectivity similar to that of the underlying substrate.

None of the above-described approaches is entirely satisfactory. It is therefore desirable to provide an improved scatterometer with better performance.

SUMMARY OF THE INVENTION

One aspect of the invention is directed towards a method of measuring one or more parameters of a diffracting structure on an underlying structure, said underlying structure having a film thickness and an optical index, comprising providing an optical index and a film thickness of the underlying structure; constructing a reference database of one or more parameters related to said diffracting structure using said optical index and film thickness of the underlying structure; and directing a beam of electromagnetic radiation at a plurality of wavelengths at said diffracting structure. The method further comprises detecting intensities or ellipsometric parameters at said plurality of wavelengths of a diffraction from said structure; and comparing said detected intensities or ellipsometric parameters to said database to determine said one or more parameters.

Another aspect of the invention is directed towards an apparatus for measuring one or more parameters of a diffracting structure on an underlying structure, said underlying structure having a film thickness and an optical index, comprising means for constructing a reference database of one or more parameters related to said diffracting structure using an optical index and a film thickness of the underlying structure; and means for directing a beam of electromagnetic radiation including energy at a plurality of wavelengths at said diffracting structure. The apparatus further comprises means for detecting intensities or ellipsometric parameters of a diffraction from said structure at said plurality of wavelengths; and means for comparing said detected intensities or ellipsometric parameters to said database to determine said one or more parameters.

Another aspect of the invention is directed towards a scatterometer for measuring a parameter of a diffracting structure of a sample, including a source which emits broadband radiation; a polarizer that polarizes the broadband radiation to produce a sampling beam sampling the structure; and means for detecting intensities or ellipsometric parameters of a diffraction from the structure over a range of wavelengths.

An additional aspect of the invention is directed towards a method for measuring one or more parameters of a diffracting structure of a sample, including providing broadband radiation; polarizing the broadband radiation to produce a sampling beam; and directing the sampling beam towards the structure. The method further comprises detecting radiation of the sampling beam that has been diffracted from the structure over a range of wavelengths; and comparing the detected radiation to a reference to determine said one or more parameters.

One more aspect of the invention is directed towards an instrument for measuring one or more parameters of a diffracting structure on an underlying structure of a sample, comprising a source of broadband radiation; a polarizer polarizing said radiation to provide a sampling beam towards the sample; and an analyzer for receiving diffracted radiation from the structure to provide an output beam. The instrument further comprises a spectrometer detecting the output beam.

One more aspect of the invention is directed towards a method for measuring one or more parameters of a diffracting structure on an underlying structure of a sample, comprising performing spectroscopic measurements on the underlying structure to determine its characteristics; constructing a reference database of one or more parameters related to said diffracting structure using characteristics of the underlying structure; and performing scatterometric measurements on the diffracting structure to obtain intensity or ellipsometric data; and comparing said intensity or ellipsometric data to the reference database to derive said one or more parameters.

Yet another aspect of the invention is directed towards an instrument for measuring a sample, comprising a spectroscopic device measuring film thickness data, and index of refraction data of the sample over a spectrum; a scatterometer measuring diffraction data from a diffracting structure of said sample over a spectrum and means for deriving physical parameters related to the structure from the film thickness data, index of refraction data, and diffraction data.

BRIEF DESCRIPTION OF THE DRAWINGS

For simplicity in description, identical components are identified by the same numerals in this application.

DETAILED DESCRIPTION OF THE PREFERRED EMBODIMENT

This invention is based on the recognition that, by measuring or otherwise obtaining characteristics such as the film thickness and optical index of the underlying films underneath the diffracting structure, the subsequent tasks of construction of a database and matching a signature of the diffracting structure to the database are much simplified. Furthermore, if spectroscopic ellipsometry is used to measure the film thickness and optical index of the underlying film(s) under the diffracting structure, an instrument which can be used for spectroscopic ellipsometry as well as for spectroscopic scatterometry may be provided for carrying out both functions. In the preferred embodiment, the spectroscopic ellipsometer and its associated spectroscopic scatterometer in the instrument may share many common optical elements to reduce the cost of the combined instrument and simplify its operation.

By first measuring the film thickness and optical refractive index of the underlying films, one no longer needs to include such parameters in the computation of the model or database and subsequent matching of signatures that much simplifies the computation task.

Figure 1A:
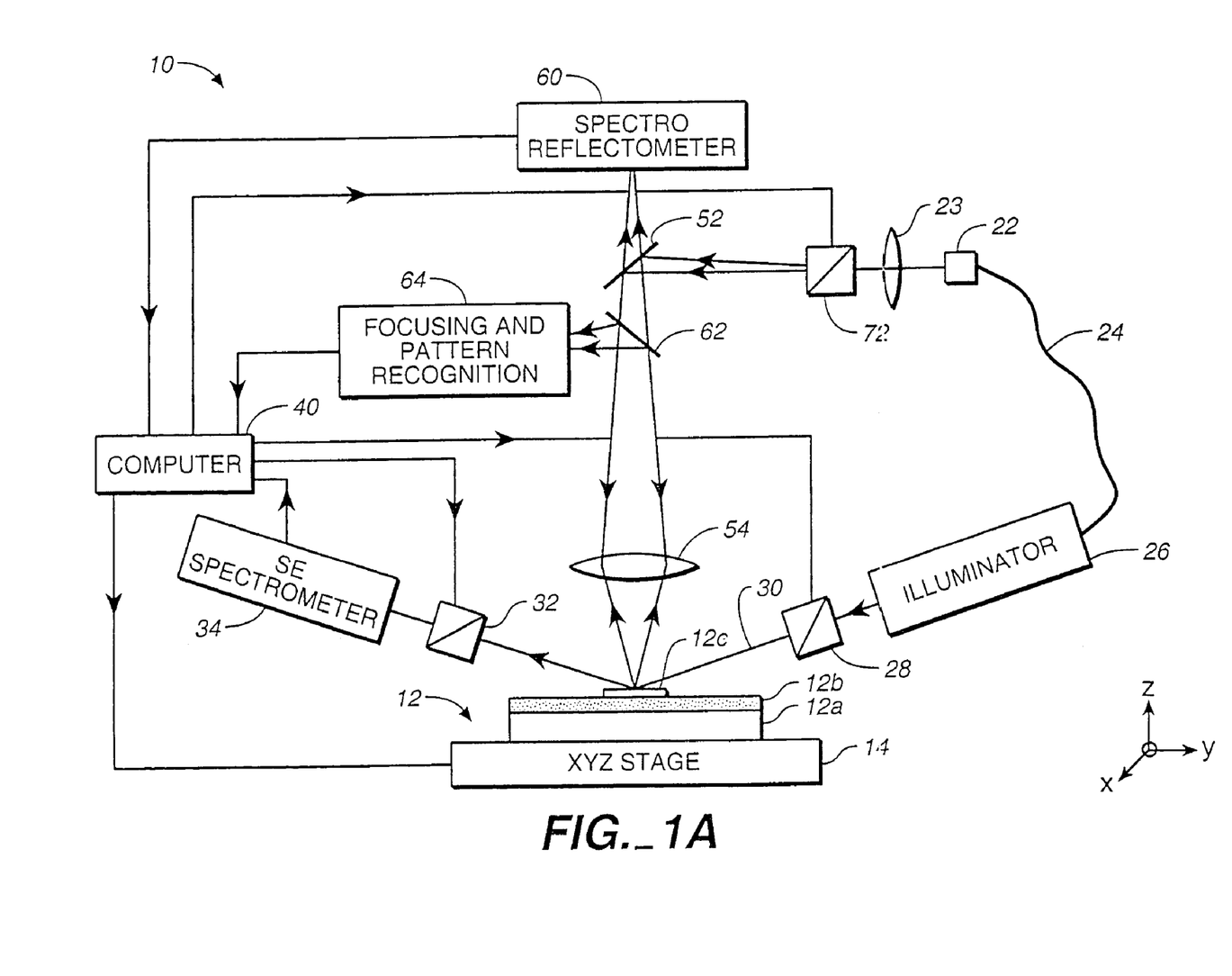
FIG. 1A is a schematic view of a spectroscopic scatterometer to illustrate the preferred embodiment of the invention.

FIG. 1A is a schematic view of a spectroscopic scatterometer system to illustrate the preferred embodiment of the invention. As shown in FIG. 1A, system 10 advantageously combines features of a spectroscopic scatterometer, spectroscopic ellipsometer and spectroscopic reflectometer. The spectroscopic reflectometer or the spectroscopic ellipsometer may be used for measuring the film thickness and refractive index of the underlying structure underneath the diffracting structure. As shown in FIG. 1A, a semiconductor wafer may comprise a silicon substrate 12a, a film 12b on the substrate and a diffracting structure 12c such as a photoresist pattern on the film, where the film is at least partially light-transmissive and has a certain film thickness and refractive index (n and k, the real and imaginary components of the index)

Figure 1B:
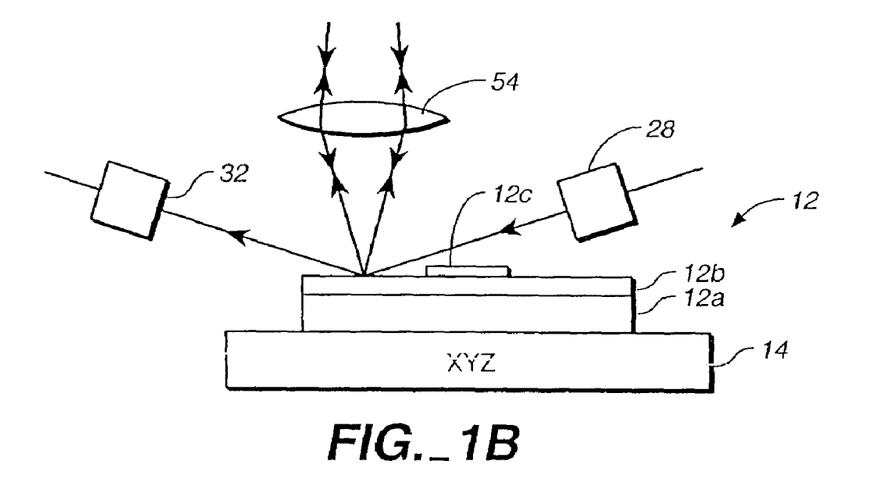
FIG. 1B is a schematic view of a portion of the spectroscopic scatterometer of FIG. 1A to illustrate the preferred embodiment of the invention.

Before the diffracting structure 12c is measured, an XYZ stage 14 is used for moving the wafer in the horizontal XY directions in order to first measure the film thickness and refractive index of the underlying structure underneath the photoresist pattern 12c. Stage 14 may also be used to adjust the z height of the wafer 12 as described below. Stage 14 moves the wafer to a position as shown in FIG. 1B so that the sampling beam of radiation illuminates a portion of film 12b away from structure 12c. In reference to FIGS. 1A, 1B, for the purpose of measuring the film thickness and refractive index of the underlying structure (12b and 12a), a broadband radiation source such as white light source 22 supplies light through a fiber optic cable 24 which randomizes the polarization and creates a uniform light source for illuminating the wafer. Preferably, source 22 supplies electromagnetic radiation having wavelengths in the range of at least 230 to 800 nm. Upon emerging from fiber 24, the radiation passes through an optical illuminator that may include a slit aperture and a focus lens (not shown). The slit aperture causes the emerging light beam to image a small area of layer 12b. The light emerging from illuminator 26 is polarized by a polarizer 28 to produce a polarized sampling beam 30 illuminating the layer 12b.

The radiation originating from sampling beam 30 that is reflected by layer 12b, passed through an analyzer 32 and to a spectrometer 34 to detect different spectral components of the reflected radiation. In the spectroscopic ellipsometry mode of system 10 for measuring film thickness and refractive index, either the polarizer 28 or the analyzer 30 is rotated (to cause relative rotational motion between the polarizer and the analyzer) when spectrometer 34 is detecting the reflected light at a plurality of wavelengths, such as those in the spectrum of the radiation source 22, where the rotation is controlled by computer 40 in a manner known to those skilled in the art. The reflected intensities at different wavelengths detected is supplied to computer 40 which computes the film thickness and n and k values of the refractive index of layer 12b in a manner known to those skilled in the art. For a description of a spectroscopic ellipsometer, please see U.S. Pat. No. 5,608,526, issued Mar. 4, 1997.

While spectroscopic ellipsometry may be preferred for measuring film thickness and refractive index, in some applications where there may only be one or two relatively thick films underneath the diffracting structure, a spectroscopic reflectometer (also known as spectroreflectometer and spectrophotometer) may be adequate for measuring the film thickness and refractive index. For this purpose, lens 23 collects and directs radiation from source 22 to a beam splitter 52, which reflects part of the incoming beam towards the focus lens 54 which focuses the radiation to layer 12b. The light reflected by the layer 12b is collected by lens 54, passes through the beam splitter 52 to a spectrometer in the spectroscopic reflectometer 60. The spectral components at different wavelengths measured are detected and signals representing such components are supplied to computer 40 for determining the film thickness and refractive index in a manner described, for example, in U.S. patent application Ser. No. 08/227,482, filed Apr. 14, 1994. Spectroscopic devices other than the spectroscopic reflectometer and spectroscopic ellipsometer may also be used for measuring the film thickness and refractive index of layer 12b and are within the scope of the invention. An example of such spectroscopic devices include the n & k Analyzer of n & k Technology Inc. of Santa Clara, Calif., and described in "Optical Characterization of Amorphous and Polycrystalline Silicon Films," by Ibok et al., reprinted from August 1995 edition of *Solid State Technology* published by PennWell Publishing Company; "Optical Dispersion Relations for Amorphous Semiconductors and Amorphous Dielectrics," by Forouhi et al., *Physical Review B*, vol. 34, no. 10, pp 7018–7026, Nov. 15, 1986; "Optical Properties of Crystalline Semiconductors and Dielectrics," by Forouhi et al.,

*Physical Review B,* vol. 38, no. 3, pp 1865–1874, Jul. 15, 1988 and U.S. Pat. No. 4,905,170.

For the purpose of adjusting the height of wafer 12 relative to the polarizer 28, analyzer, 32 to achieve proper focus in the spectroscopy ellipsometry measurement, or relative to the focus lens 54 and spectroscopic reflectometer 60 in the spectroreflectometer measurement, the height of the wafer may need to be adjusted by means of stage 14 prior to the measurement. For this purpose, a portion of the radiation reflected by layer 12b (or layer 12c in the description that follows) and collected by lens 54 is reflected by a beamsplitter 62 towards a focusing and pattern recognition block 64 for comparing the reflected image to a pattern. Block 62 then sends information concerning the comparison to computer 40 which controls stage 14. Stage 14, in turn, moves the wafer 12 up or down in the vertical or Z direction in order to move wafer 12 to a proper height relative to the optical components of system 10.

Once the film thickness and refractive index of the one or more films underneath the diffracting structure 12c have been so measured, a reference database may now be constructed by means of computer 40. Where the film thickness and refractive index of the one or more films underneath the diffracting structure 12c are known to begin with, or can be estimated, it is possible to omit the step of measuring these quantities. To construct the reference database, characteristics concerning the diffracting structure 12c may be parameterized and the parameters database is defined by allowing an unknown grating parameter of the structure, such as linewidth, height and wall angle to vary over a certain range. This is illustrated by reference to FIG. 2.

Figure 2:
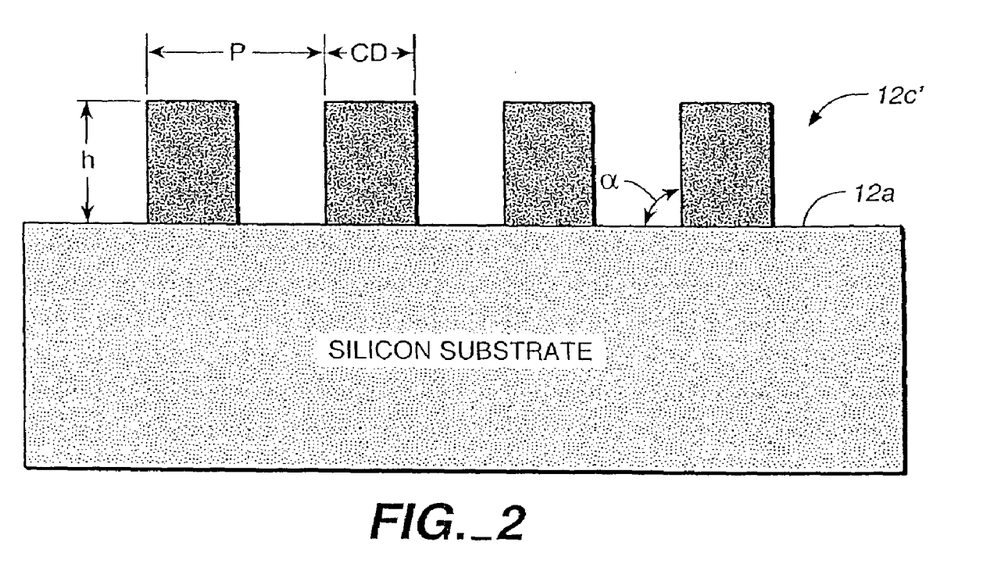
FIG. 2 is a cross-sectional view of a semiconductor wafer including a line pattern of photoresist on a-bare silicon substrate useful for illustrating the invention.

FIG. 2 is a cross-sectional view of a semiconductor wafer comprising a silicon substrate 12a and a diffracting structure 12c' having a linewidth CD, pitch p, height h, and wall angle $\alpha$ as shown in FIG. 2. Thus, the grating shape parameters that can be parameterized and varied over a certain range include CD, h and $\alpha$. A rigorous diffraction model, such as the model method by modal expansion (MMME), is used to calculate the theoretical diffracted light fingerprint from each grating in the parameter space, and a statistical prediction algorithm such as Partial-Leased-Squares (PLS) or Minimum-Mean-Square-Error (MMSE) is trained on this theoretical calibration data. For a description of the MMME, please see "Convergence of the Coupled-wave Method for Metallic Lamellar Diffraction Gratings," by Li et al., *Journal of the Optical Society of America A* Vol. 10, No. 6, pp. 1184–1189, June 1993; and "Multilayer Modal Method for Diffraction Gratings of Arbitrary Profile, Depth, and Permittivity," by Li et al., *Journal of the Optical Society of America A* Vol. 10, No. 12, pp. 2582–2591, December 1993.

Instead of using the MMME, the grating shape parameters can also be parameterized using rigorous coupling waveguide analysis ("RCWA"). Such method is described, for example, in "Rigorous coupled-wave analysis of planar-grating diffraction," by M. Moharam et al., *J. Opt. Soc. Am.,* Vol. 71, No. 7, July 1981, pp. 811–818, "Stable implementation of the rigorous coupled-wave analysis for surface-relief gratings: enhanced transmittance matrix approach," by M. Moharam et al., *J. Opt. Soc. Am. A,* Vol. 12, No. 5, May 1995, pp. 1077–1086, and "Analysis and Applications of Optical Diffraction by Gratings," T. Gaylord et al., *Proceedings of the IEEE,* Vol. 73, No. 5, May 1985, pp. 894–937.

Where more than one grating shape parameter is varied, the calculation of fingerprints may be performed by varying only one parameter at a time while keeping the other parameters at selected constant values within selected ranges. Then another parameter is allowed to vary and so on. Subsequently, this prediction algorithm is used to determine the values of the parameters that correspond to the fingerprint measured from layer 12c'.

Since the film thickness and optical indices of any film underlying diffracting structure 12c or 12c' are known from the spectroscopic ellipsometry or spectroreflectometry measurements, or are otherwise known, these values may be used in construction of the reference database so that the film thickness and refractive index need not be parameters in the database. This greatly reduces the number of variables in the parameter space and also greatly reduces the number of signatures that need to be calculated for the reference database. Thus, compared to the 2-$\Theta$ scatterometry method where such variables need to be taken into account in the parameter space and the calculation of signatures, this invention enables a smaller database to be used when searching for solutions. Furthermore, due to the number of variables that are parameterized in such 2-$\Theta$ scatterometry method, there may be multiple solutions which causes difficulties in obtaining a correct solution. By reducing the size of the database, this invention enables unique solutions to be found in most cases. In this manner, this invention reduces the computation time by many orders of magnitude compared to 2-$\Theta$ scatterometry.

The process for measuring the signature from layer 12c and 12c' will now be described in reference to FIG. 1A. As described above, stage 14 moves wafer 12 so that the sampling beam 30 illuminates an area of the underlying film 12b without illuminating any portion of the diffracting structure 12c. Now in order to measure structure 12c, the computer 40 causes stage 14 to move the wafer along a direction in the XY plane so that the sampling beam 30 impinges on layer 12c (or 12c' in FIG. 2). Broadband radiation from source 22 is polarized by polarizer 28 into a polarized broadbeam sampling beam 30. A diffraction of beam 30 is supplied to spectrometer 34 which measures substantially simultaneously the radiation intensities at different wavelengths of a diffraction from structure 12c, such as at wavelengths across the spectrum of radiation source 22. In the preferred embodiment, the zeroth diffraction order intensity is measured, although for some structures, measurement of higher diffraction order intensities may also be feasible. The process just described is the scatterometric measurement mode of system 10.

Zeroth or higher diffraction order intensities at different wavelengths detected by spectrometer 34 are supplied to computer 40 for analysis and determination of a signature of structure 12c or 12c'. This signature is then compared to those precomputed in the reference database in the manner described above. The grating shape parameters of the signature in the reference database that matches the measured signature of structure 12c or 12c' are then the grating shape parameters of the structure.

In the scatterometric measurement mode, analyzer 32 may be simply removed from the optical path from structure 12c to spectrometer 34. Alternatively, polarizer 28 and analyzer 32 may be controlled by means of computer 40 so that polarizer 28 passes radiation of a certain polarization and analyzer 32 is oriented to pass radiation of the same polarization as that passed by polarizer 28. This invention is based on the discovery that, where the incidence plane of the beam 30 is substantially normal to the grating 12c, the sensitivity of scatterometric measurements is improved if polarizer 28 is oriented to supply a sampling beam 30 polarized in the TE mode (S-polarized) and analyzer 32 is oriented to pass light in the TE mode. Alternatively, where the incidence plane of the beam 30 is substantially parallel to the grating 12c, the sensitivity of scatterometric measurements is improved if polarizer 28 is oriented to supply a sampling beam 30 polarized in the TM mode (P-polarized) and analyzer 32 is oriented to pass light in the TM mode.

If more than one diffracting structure having different shape parameters are present on wafer 12, stage 14 may be controlled by computer 40 to move wafer 12 so that the sampling beam 30 is directed towards each of such diffracting structures one at a time. System 10 is then operated in the scatterometric measuring mode to obtain signatures from each of such diffracting structures. The signature of each diffracting structure may then be matched with a signature in the reference database in order to obtain the grating shape parameters of such structure. It will be noted that, where measurement of the characteristics of the underlying structure (12a, 12b) is necessary, this will need to be performed only once for each wafer and the reference database will need to be constructed only once for the wafer as well. After these have been accomplished, the scatterometric measurements of the different diffracting structures on wafer 12 may be performed quickly and the signatures of each diffracting structure matched to the reference database expeditiously. As noted above, since the reference database contains a smaller number of signatures, the matching or prediction speed of the grating shape parameters of the different diffracting structures on wafer 12 is greatly increased. This makes real time and in-line measurements of the diffracting structures possible. In some applications, a number of semiconductor wafers made by the same process have the same underlying structure underneath the diffraction structures; these underlying structures of the different wafers may have substantially the same film thicknesses and indices of refraction. If this is the case, the above-described process for measuring film thickness and index refraction and the construction of the reference database may need to be performed only once for the entire batch of wafers made by the same process, if the tolerance of the process is known. This further speeds up the measurement and calculation process.

As compared to 2-Θ scatterometry, the spectroscopic scatterometer of this invention measures diffraction and a number of wavelengths simultaneously. This is in contrast to 2-Θ scatterometry where the user takes a measurement of the diffraction at one angle of incidence at a time. Such feature also speeds up the measurement process. It will also be noted that the above-described reference database is constructed without the use of reference samples. Thus, the user does not have to make reference wafers having diffracting structures analogous to the one being measured or having to take measurements from such reference samples before a database can be constructed. Furthermore, a rigorously radical model such as MMME is used to achieve accurate results.

Preferably, in the spectroscopic ellipsometry mode and the scatterometric measurement mode, sampling beam 30 is directed towards wafer 12 at an oblique angle to layer 12b and 12c. Sampling beam 30 is preferably at an oblique angle in the range of 40 to 80° and more preferably in the range of 60 to 80° for measurement of silicon wafers, from a normal to the layers on the wafer 12. A particularly preferred angle of incidence from the normal is about 76° which is substantially the Brewster angle for silicon. In system 10, the spectroscopic ellipsometer and spectroscopic scatterometer advantageously employ many common optical elements, such as the broadband source 22, fiber 24, illuminator 26, polarizer 28 and spectrometer 34. This simplifies the design of system 10, reduces cost and simplifies its operation.

The process for adjusting the height of wafer 12 relative to the optical components in the spectroreflectometry and spectroscopic ellipsometry modes has been described above. However, when light reflected from beamsplitter 52 is directed towards a diffracting structure such as 12c, it is preferable for the light so reflected to be polarized and to have the same polarization as that in sampling beam 30 when the height of the wafer 12 is adjusted. For this purpose, radiation supplied by source 22 is passed through a polarizer 72 before it is directed to beamsplitter 52. The optical axis of polarizer 72 is controlled by computer 40 so that it has the same orientation as the optical axis of polarizer 28 when the focusing and pattern recognition block 64 is used to detect radiation reflected from structure 12c and stage 14 is controlled by computer 40 to adjust height of the wafer until it is at the proper height relative to the sampling beam 30. Polarizer 72 does not affect the height adjustment process during the spectroreflectometry and spectroscopic ellipsometry modes or the spectroscopic reflectometry measurements. The polarized radiation detected by spectroscopic reflectometer 60 may also be used to normalize the intensity measurement in the scatterometer mode described above at an oblique angle to reduce the effects of intensity variations of source 22.

Figure 3A:
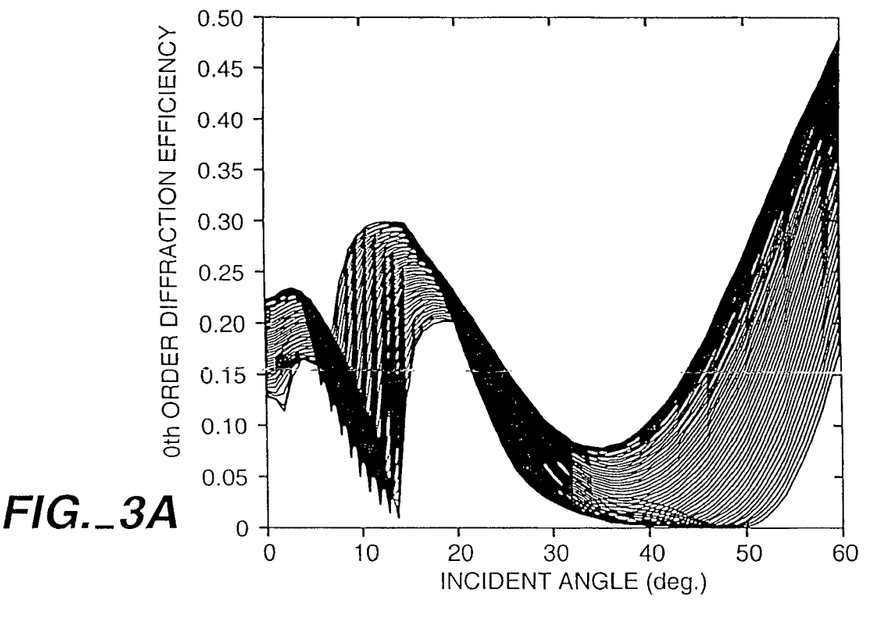
FIG. 3A is a graphical plot of the intensity of the zeroth diffraction order as 51 different functions of the angle of incidence of the illuminating light beam in a 2-Θ scatterometer, where the nominal linewidth is assumed to be 250 nanometers, and the 51 functions are obtained assuming linewidths from 225 to 275 nanometers, at 1 nanometer steps, for comparison with predicted results of the invention.

FIG. 3A is a graphical plot of the intensity of the zeroth diffraction order as 51 functions of the angle of incidence of the illuminating light beam in a 2-Θ scatterometer measuring structure 12c' of FIG. 2, where the nominal linewidth is assumed to be 250 nm, and the 51 functions are obtained assuming linewidths from 225 to 275 nanometers, at 1 nanometer steps. The incidence angles used in a calculation of the graphical plot in FIG. 3A varies from 0 to 60° with an uniform increment of 1°, which results in 61 datapoints per signature curve. The light beam is assumed to be TE polarized and the wavelength was 0.6328 microns.

Figure 3B:
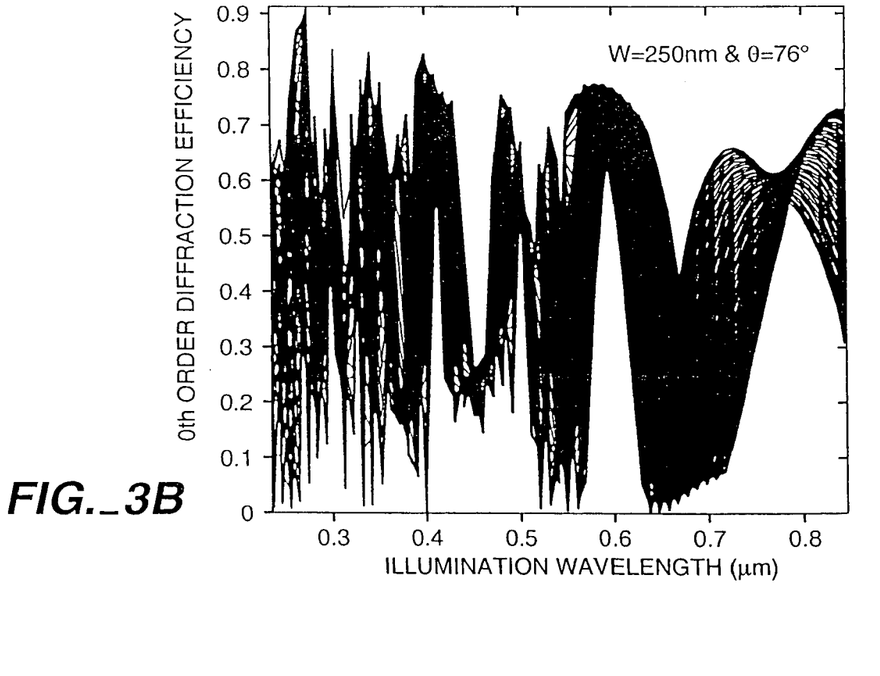
FIG. 3B is a graphical plot of the intensity of the zeroth diffraction order as 51 different functions of the wavelength of the illuminating light beam according to the invention where the nominal linewidth is assumed to be 250 nanometers, and the 51 functions are obtained assuming linewidths from 225 to 275 nanometers, at 1 nanometer steps, for comparison with predicted results of the invention.
Figure 3C:
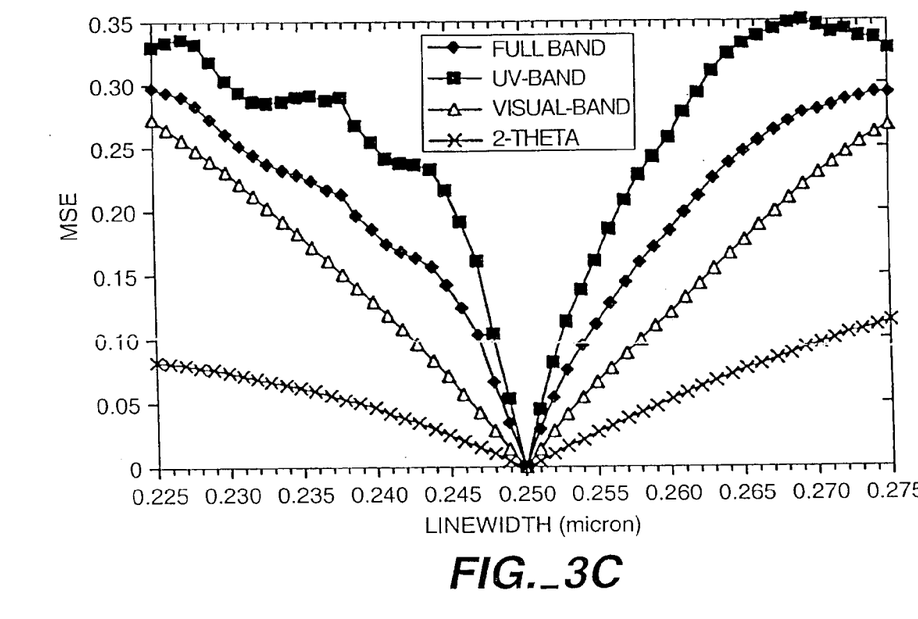
FIG. 3C is a plot of the means square error difference measurement as a function of linewidth, between the signature generated for the grating having the nominal linewidth of 250 nanometers and other signatures obtained for other linewidths using 2-Θ scatterometry, and using the preferred embodiment of this invention over a full range of the spectrum and over UV and visual wavelength bands of the full spectrum useful for illustrating the invention.

FIG. 3B is a graphical plot of the intensity of zeroth diffraction order as a function of the wavelength of the illuminating light beam according to the invention used for measuring structure 12c' of FIG. 2 where the nominal linewidth is assumed to be 250 nm, and the 51 functions are obtained assuming linewidths from 225 to 275 nanometers, at 1 nanometer steps. These 51 functions are obtained by means of the MMME model method rigorous diffraction method described above, making use of the known or measured index of refraction and film thickness information. These curves are used in comparison with measured results of the invention to predict linewidth of the measured structure. The intensity of the zeroth order is calculated as a function of the wavelength of the illuminating light beam and the wavelengths used in the calculation varies from 0.23 to 0.850 microns with an uniform increment of 0.01 micron which results in 63 datapoints per signature curve. The light beam is assumed to be TE polarized and is illuminated at an oblique angle of 76° from the normal. FIG. 3C is a plot of the mean squares error difference measurement as a function of linewidth, between the signature generated for the grating having the linewidth of 250 nm and other signatures obtained at other linewidths using 2-Θ scatterometry. FIG. 3C also shows plots of the mean squares error difference measurement as a function of linewidth, between the signature generated for the grating having the linewidth of 250 nm and other signatures obtained at other linewidths, and using the preferred embodiment of this invention over a full range of the spectrum as well as over ultraviolet (UV) and visual wavelength bands of the full spectrum. As will be evident from FIG. 3C, the spectroscopic scatterometer of this invention is more sensitive than the 2-Θ scatterometer. The mean square area difference for 1 nm linewidth (CD) sensitivity are shown by Tables 1 and 2 below.

TABLE 1

MSE Different for 1 nm CD Sensitivity

| CD (nm) | Full Band | UV Band | Visual Band | 2-θ |
|---|---|---|---|---|
| 250 | 0.0339 | 0.0528 | 0.0142 | 0.0051 |

TABLE 2

MSE Ratio With Respect to 2-θ

| CD (nm) | Full Band | UV Band | Visual Band |
|---|---|---|---|
| 250 | 6.62 | 10.31 | 2.78 |

From FIG. 3C, it is also evident that the sensitivity may be higher if only data collected using radiation at a sub-band of the full spectrum is used for matching the signature. Thus, even though the spectrometer 34 records the diffraction for the full range of wavelengths in the spectrum, sensitivity may be improved if only the diffraction at wavelengths in the ultraviolet (UV) band is used to construct the measured signatures from the diffracting structure of 12c and 12c'. Such signatures are then matched to signatures in the database calculated for the UV band as well. From FIG. 3B, it is noted that each of the curves is a function characterizing a particular signature of a grating. While in FIG. 3C, information in the ultraviolet band may provide higher sensitivity compared to the visual band or the full band, information in a different portion of the spectrum may provide better sensitivity for gratings of other shapes and dimensions. All such variations are within the scope of the invention.

Figure 4A:
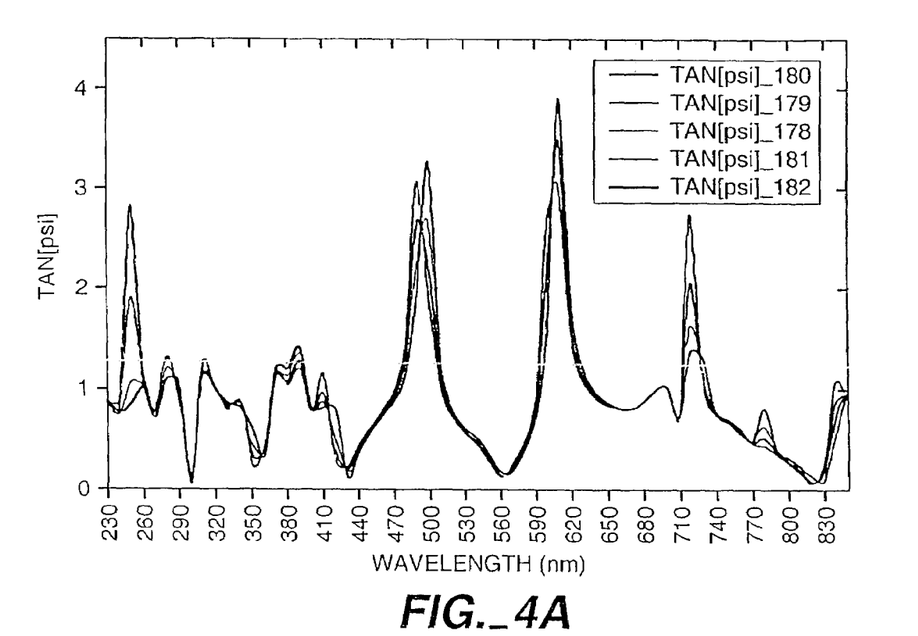
FIG. 4A is a graphical plot of the intensity of an ellipsometric parameter tan(psi) as 5 different functions of the wavelength of the illuminating light beam according to the invention where the nominal linewidth is assumed to be 180 nanometers, and the 5 functions are obtained assuming linewidths at 178, 179, 180, 181, 182 nanometers, for comparison with predicted results of the invention.
Figure 4B:
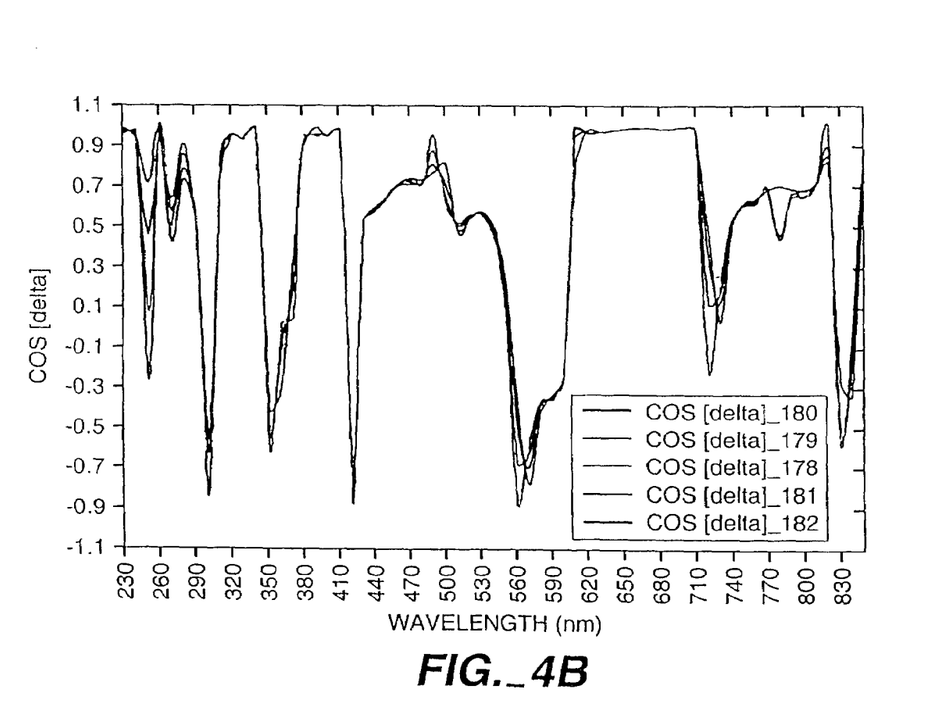
FIG. 4B is a graphical plot of the intensity of an ellipsometric parameter cos(delta) as 5 different functions of the wavelength of the illuminating light beam according to the invention where the nominal linewidth is assumed to be 180 nanometers, and the 5 functions are obtained assuming linewidths at 178, 179, 180, 181, 182 nanometers, for comparison with predicted results of the invention.
Figure 5:
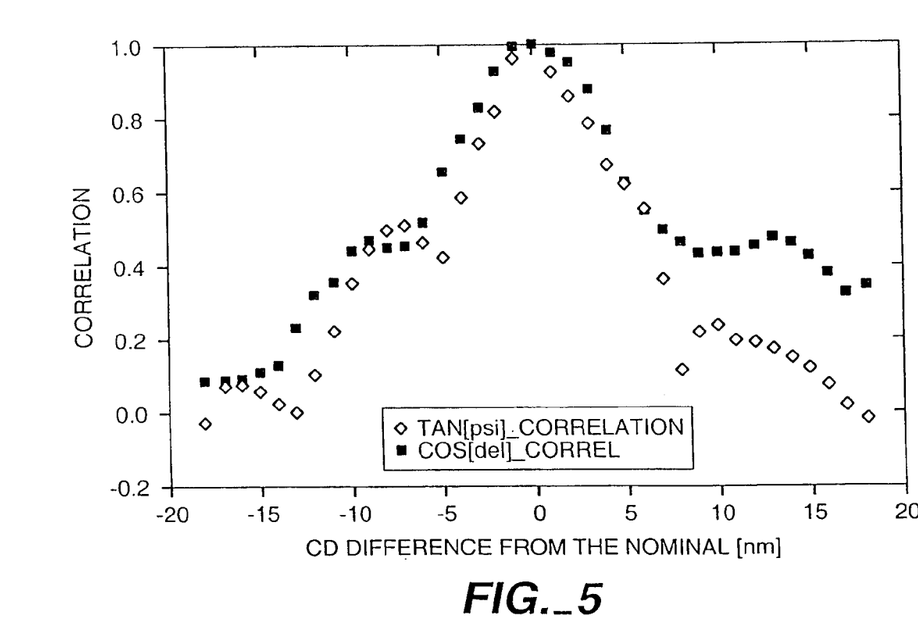
FIG. 5 is a plot of two sets of correlation functions between the signature for the grating having the nominal linewidth of 180 nanometers and other signatures for gratings at other linewidths, one set obtained using tan(psi) and the other set obtained using cos(delta).

Another aspect of the invention is based on the observation that, instead of detecting the intensity of the zero, first or other order of diffraction from structure 12c or 12c', the apparatus 10 of FIG. 1A may be used to detect ellipsometric parameters of such order diffraction from the structure for determining one or more parameters of the diffracting structure. In other words, during the scatterometer mode, computer 40 controls polarizer 28 and analyzer 32 to cause relative rotation and motion between them, and system 10 is used for measuring ellipsometric parameters such as tan (psi) and cos (delta) adds a plurality of wavelengths, such as at wavelengths in the spectrum of radiation source 22. With either known or measured index or refraction and film thickness information of the one or more underlying films underneath the structure 12c or 12c', the MMME model method described above may be used to construct a database of tan (psi) and cos (delta) as functions of wavelength, as illustrated in FIGS. 4A and 4B, corresponding to different values of parameters of the structure 12c or 12c'. Thus as shown in FIG. 4A, the model may be used to construct five functions for tan (psi) as functions of wavelength at five different linewidths. FIG. 4B illustrates a similar plot for the ellipsometric parameter cos (delta). The nominal linewidth is 180 nanometers. By measuring the two ellipsometric parameters of structure 12c or 12c' by means of system 10, the measured functions may be compared to those in FIGS. 4A and 4B to find the best fit. The sensitivity in using the ellipsometric parameters is illustrated in FIG. 5. FIG. FIG. 5 is a plot of the correlation between the ellipsometric parameters corresponding to the nominal 180 nanometer value and those corresponding to the remaining four line width values. Other than the above noted differences, in this aspect of the invention where ellipsometric parameters are used for determining characteristics of the structure 12c, 12c', the system 10 operates in a manner and shares the same advantages essentially as those described above for measuring intensity of diffraction in determining characteristics of the structure 12c, 12c'. For some applications, measuring the ellipsometric parameters may offer higher sensitivity.

While the construction of database is illustrated above by reference to functions corresponding to different linewidths, it will be understood that similar functions may be constructed using the model for other parameters of the structure 12c or 12c', such as height or wall angle of the structure. Such and other variations are within the scope of the invention.

While the invention has been described by reference to various embodiments, it will be understood that different changes and modifications may be made without departing from the scope of the invention which is to be defined only by the appended claims and their equivalents.

What is claimed is:

1. An apparatus for measuring a sample with a periodic diffracting structure, said apparatus comprising:
a reflectometer; and
an ellipsometer which comprises:
a source of broadband radiation;
a polarizer polarizing said radiation to provide a sampling beam towards the sample;
an analyzer receiving radiation from the sampling beam diffracted by the periodic diffracting structure to provide an output beam;
a spectrometer detecting intensity data from the output beam simultaneously at a plurality of wavelengths; and
a computer deriving from the intensity data a characteristic of the sample related to the structure, said characteristic including at least one of the following: shape of line, line width, period and side wall angle of the structure.

2. The apparatus of claim 1, said sample having a layer associated with the structure, said apparatus further comprising a device causing the polarizer or analyzer to rotate when the sampling beam is directed to the associated layer and not to the diffracting structure, and causing the polarizer and analyzer not to rotate when the sampling beam is directed to the diffracting structure.

3. The apparatus of claim 2, wherein said device causes the polarizer to provide and the analyzer to pass radiation having substantially the same polarization.

4. The apparatus of claim 1, said sample having a layer associated with the structure, further comprising a device causing the polarizer or analyzer to rotate when the sampling beam is directed to the associated layer without the diffracting structure and causing the polarizer or analyzer not to rotate when the sampling beam is directed to the diffracting structure.

5. The apparatus of claim 1, further comprising a focusing element providing polarized radiation, and a device that adjusts height of the diffraction structure relative to the polarizer and detector in response to the polarized radiation provided by the focusing element.

6. The apparatus of claim 5, wherein the polarized radiation provided by the focusing element has substantially the same polarization as the sampling beam.

7. The apparatus of claim 1, wherein the sampling beam is provided at an oblique angle to a surface of the sample.

8. The apparatus of claim 1, wherein the computer derives the characteristic using a database.

9. The apparatus of claim 1, wherein the computer computes ellipsometric parameters from the intensity data in deriving the characteristic of the sample related to the structure.

10. The apparatus of claim 1, wherein the analyzer analyzes radiation from only a single order diffraction from the periodic diffracting structure.

11. The apparatus of claim 10, wherein the single order diffraction is the zeroth or the first order.

12. The apparatus of claim 1, wherein said source includes an optical fiber.

13. The apparatus of claim 1, said plurality of wavelengths comprising ultraviolet wavelengths.

14. The apparatus of claim 1, wherein said reflectometer and ellipsometer employ common optical elements, said common elements comprising a broadband radiation source, a polarizer and a spectrometer.

15. The apparatus of claim 1, wherein said computer derives the characteristic of the sample from the intensity data at some but not all of said plurality of wavelengths.

16. The apparatus of claim 15, said some but not all of said plurality of wavelengths comprising ultraviolet wavelengths.

17. The apparatus of claim 1, said reflectometer and ellipsometer measuring an optical index and film thickness of the sample.

18. An method for measuring a sample with a periodic diffracting structure, said method comprising:
    performing a measurement on the sample by means of a reflectometer and an ellipsometer, said performing comprising:
    polarizing broadband radiation to provide a sampling beam towards the sample;
    analyzing radiation from the sampling beam diffracted by the periodic diffracting structure to provide an output beam;
    detecting intensity data from the output beam simultaneously at a plurality of wavelengths; and
    deriving from the intensity data a characteristic of the sample related to the structure, said characteristic including at least one of the following: shape of line, line width, period and side wall angle of the structure.

19. The method of claim 18, wherein the sampling beam is provided at an oblique angle to a surface of the sample.

20. The method of claim 18, wherein the deriving derives the characteristic using a database.

21. The method of claim 18, wherein the deriving computes ellipsometric parameters from the intensity data in deriving the characteristic of the sample related to the structure.

22. The method of claim 18, wherein the analyzing analyzes radiation from only a single order diffraction from the periodic diffracting structure.

23. The method of claim 22, wherein the single order diffraction is the zeroth or the first order.

24. The method of claim 18, said plurality of wavelengths comprising ultraviolet wavelengths.

25. The method of claim 18, wherein said deriving derives the characteristic of the sample from the intensity data at some but not all of said plurality of wavelengths.

26. The method of claim 25, said some but not all of said plurality of wavelengths comprising ultraviolet wavelengths.

27. The method of claim 18, further comprising measuring an optical index and film thickness of the sample.

28. The method of claim 18, further comprising using the characteristic of the sample in wafer process monitoring, closed-loop control or focus-exposure control in photolithography.

29. The method of claim 18, wherein said polarizing polarizes the broadband radiation so that the sampling beam is in the TE or TM mode, and the detecting detects radiation in the TE or TM mode.

30. The method of claim 18, wherein said sample comprises a plurality of periodic diffracting structures and a substrate comprising one or more layers associated with the structures, wherein said spectroscopic measurements measures film thickness or index of refraction information of said one or more layers only once, and wherein said scatterometric measurements measure each of the structures to obtain data.

31. An apparatus for measuring a sample with a periodic diffracting structure, said apparatus comprising:
    a source of broadband radiation providing a sampling beam towards the sample, said radiation having a range of wavelengths;
    a detector detecting radiation in said range of wavelengths from the sampling beam diffracted by the periodic diffracting structure; and
    a computer computing from the output information concerning the structure from the detected diffracted radiation over said range of wavelengths, and deriving a characteristic of the structure from information in the detected diffracted radiation over only a portion of said range of wavelengths, wherein information concerning the structure from the detected diffracted radiation over said portion of said range of wavelengths provides higher sensitivity in deriving said characteristic of the structure than information concerning the structure from the detected diffracted radiation over other portions of said range of wavelengths.

32. The apparatus of claim 31, wherein the computer derives said characteristic by matching the detected diffracted radiation over said portion of said range of wavelengths to signatures in a database.

33. The apparatus of claim 31, said detector comprising an analyzer, said sample having a layer associated with the structure, said apparatus further comprising a polarizer polarizing radiation in said sampling beam before it is provided towards the sample, and a device causing the polarizer or analyzer to rotate when the sampling beam is directed to the associated layer and not to the diffracting structure, and causing the polarizer and analyzer not to rotate when the sampling beam is directed to the diffracting structure.

34. The apparatus of claim 33, wherein said device causes the polarizer to provide and the analyzer to pass radiation having substantially the same polarization.

35. The apparatus of claim 31, said detector comprising an analyzer, said sample having a layer associated with the structure, said apparatus further comprising a polarizer polarizing radiation in said sampling beam before it is provided towards the sample, said apparatus further comprising a device causing the polarizer or analyzer to rotate when the sampling beam is directed to the associated layer without the diffracting structure and causing the polarizer or analyzer not to rotate when the sampling beam is directed to the diffracting structure.

36. The apparatus of claim 31, wherein the sampling beam is provided at an oblique angle to a surface of the sample.

37. The apparatus of claim 31, wherein the computer derives the characteristic using a database.

38. The apparatus of claim 37, wherein the computer derives shape of lines, linewidth, pitch, height or side wall angle of the structure.

39. The apparatus of claim 31, wherein the computer computes ellipsometric parameters from the intensity data in deriving the characteristic of the structure.

40. The apparatus of claim 31, wherein the detector detects radiation from only a single order diffraction from the periodic diffracting structure.

41. The apparatus of claim 40, wherein the single order diffraction is the zeroth or the first order.

42. An method for measuring a sample with a periodic diffracting structure, said method comprising:
   providing a sampling beam of broadband radiation towards the sample, said radiation having a range of wavelengths;
   detecting radiation in said range of wavelengths from the sampling beam diffracted by the periodic diffracting structure; and
   computing from the output information concerning the structure from the detected diffracted radiation over said range of wavelengths, and deriving a characteristic of the structure from information in the detected diffracted radiation over only a portion of said range of wavelengths, wherein information concerning the structure from the detected diffracted radiation over said portion of said range of wavelengths provides higher sensitivity in deriving said characteristic of the structure than information concerning the structure from the detected diffracted radiation over other portions of said range of wavelengths.

43. The method of claim 42, wherein the computing derives said characteristic by matching the detected diffracted radiation over said portion of said range of wavelengths to signatures in a database.

44. The method of claim 42, wherein the sampling beam is provided at an oblique angle to a surface of the sample.

45. The method of claim 42, wherein the computing derives the characteristic using a database.

46. The method of claim 45, wherein the computing derives shape of lines, linewidth, pitch, height or side wall angle of the structure.

47. The method of claim 42, wherein the computing computes ellipsometric parameters from the intensity data in deriving the characteristic of the structure.

48. An apparatus for measuring a sample with a periodic diffracting structure, comprising:
   a device measuring data related to film thickness and index of refraction of the sample said device comprising a spectroscopic reflectometer employing polarized radiation for adjusting height of the sample relative to the device and instrument; and
   an instrument measuring intensity or ellipsometric diffraction data from the periodic diffracting structure of said sample, wherein said device or said instrument use(s) broadband radiation in the measurement(s).

49. The apparatus of claim 48, said device being a spectroscopic ellipsometer or spectroscopic reflectometer.

50. The apparatus of claim 48, said device employing polarized radiation.

51. The apparatus of claim 48, said device and instrument employing one or more common optical elements, said elements comprising a polarizer.

52. The apparatus of claim 48, said device and said instrument employing one or more common optical elements, said elements comprising a broadband radiation source.

53. The apparatus of claim 48, wherein measurements of said instrument are performed substantially simultaneously at a plurality of wavelengths.

54. The apparatus of claim 48, further comprising an element constructing a reference database related to said film thickness and index of refraction of said sample over a spectrum of wavelengths, said instrument directing to the structure a beam of radiation having wavelengths that comprise said spectrum and detecting intensity or ellipsometric data over said spectrum of wavelengths.

55. The apparatus of claim 48, said instrument directing to the structure a beam of radiation having wavelengths within a range and detecting intensity or ellipsometric data over said range, wherein said instrument comprises a processor that derives a characteristic of the structure from intensity or ellipsometric data at wavelengths in a selected portion of the range.

56. The apparatus of claim 55, said processor deriving the characteristic of the structure by comparing intensity or ellipsometric data at wavelengths in the selected portion of the range with information in a reference database.

57. The apparatus of claim 56, said processor constructing the reference database from data related to said film thickness and index of refraction of said sample over a spectrum.

58. The apparatus of claim 48, said sample having a layer associated with the structure, said device measuring the layer and the instrument measuring the diffracting structure.

59. The apparatus of claim 48, said instrument comprising:
   a source of broadband radiation;
   a polarizer polarizing said radiation to provide a sampling beam towards the sample;
   an analyzer receiving radiation from the sampling beam diffracted by the periodic diffracting structure to provide an output beam;
   a spectrometer detecting intensity data from the output beam simultaneously at a plurality of wavelengths; and
   a computer deriving from the intensity data a characteristic of the sample related to the structure.

60. The apparatus of claim 59, said sample having a layer associated with the structure, said instrument further comprising a device causing the polarizer or analyzer to rotate when the sampling beam is directed to the associated layer and not to the diffracting structure, and causing the polarizer and analyzer not to rotate when the sampling beam is directed to the diffracting structure.

61. The apparatus of claim 60, wherein said device causes the polarizer to provide and the analyzer to pass radiation having substantially the same polarization.

62. The apparatus of claim 48, said sample having a layer associated with the structure, further comprising a device causing the polarizer or analyzer to rotate when the sampling beam is directed to the associated layer without the diffracting structure and causing the polarizer or analyzer not to rotate when the sampling beam is directed to the diffracting structure.

63. The apparatus of claim 48, wherein the sampling beam is provided at an oblique angle to a surface of the sample.

64. The apparatus of claim 48, wherein said computer derives a characteristic of the structure from the intensity or ellipsometric data.

65. The apparatus of claim 64, wherein the computer derives the characteristic using a database.

66. The apparatus of claim 64, wherein the computer derives shape of lines, linewidth, pitch, height or side wall angle of the structure.

67. An method for measuring a sample with a periodic diffracting structure, comprising:
   (a) measuring data related to film thickness and index of refraction of the sample; and
   (b) measuring intensity or ellipsometric diffraction data from the periodic diffracting structure of said sample, wherein said measuring in (a) or (b) uses broadband radiation, said measuring in (b) comprising:
   polarizing broadband radiation to provide a sampling beam towards the sample;
   analyzing radiation from the sampling beam diffracted by the periodic diffracting structure to provide an output beam; and
   detecting intensity data from the output beam simultaneously at a plurality of wavelengths, wherein said measuring in (a) and (b) are performed by means of a reflectometer and an ellipsometer.

68. The method of claim 67, wherein the measuring in (a) is performed by means of a spectroscopic ellipsometer or spectroscopic reflectometer.

69. The method of claim 67, wherein the measuring in (b) is performed employing broadband and polarized radiation.

70. The method of claim 67, wherein the measuring in (b) is performed substantially simultaneously at a plurality of wavelengths.

71. The method of claim 67, further comprising constructing a reference database related to said film thickness and index of refraction of said sample over a spectrum of wavelengths, wherein the measuring in (b) directs to the structure a beam of radiation having wavelengths that comprise said spectrum and detects intensity or ellipsometric data over said spectrum of wavelengths.

72. The method of claim 67, said measuring in (b) directing to the structure a beam of radiation having wavelengths within a range and detecting intensity or ellipsometric data over said range, said method further comprising deriving a characteristic of the structure from intensity or ellipsometric data at wavelengths in a selected portion of the range.

73. The method of claim 72, wherein said deriving derives the characteristic of the structure by comparing intensity or ellipsometric data at wavelengths in the selected portion of the range with information in a reference database.

74. The method of claim 72, further comprising constructing the reference database from data related to said film thickness and index of refraction of said sample over a spectrum.

75. The method of claim 67, said sample having a layer associated with the structure, said measuring in (a) measuring the layer and said measuring in (b) measuring the diffracting structure.

76. The method of claim 67, wherein the sampling beam is provided at an oblique angle to a surface of the sample.

77. The method of claim 67, further comprising a deriving a characteristic of the structure from the intensity or ellipsometric data.

78. The method of claim 77, wherein the deriving derives the characteristic using a database.

79. The method of claim 77, wherein the deriving derives shape of lines, linewidth, pitch, height or side wall angle of the structure.

80. The method of claim 42, wherein the detecting detects radiation from only a single order diffraction from the periodic diffracting structure.

81. The method of claim 80, wherein the single order diffraction is the zeroth or the first order.

82. The method of claim 67, said plurality of wavelengths comprising ultraviolet wavelengths.

83. The method of claim 67, further comprising measuring an optical index and film thickness of the sample.

84. The method of claim 67, further comprising deriving a characteristic of the sample from the intensity data and using the characteristic of the sample in wafer process monitoring, closed-loop control or focus-exposure control in photolithography.

85. The method of claim 67, wherein said polarizing polarizes the broadband radiation so that the sampling beam is in the TE or TM mode, and the detecting detects radiation in the TE or TM mode.

86. The method of claim 67, wherein said sample comprises a plurality of periodic diffracting structures and a substrate comprising one or more layers associated with the structures, wherein said spectroscopic measurements measures film thickness or index of refraction information of said one or more layers only once, and wherein said scatterometric measurements measure each of the structures to obtain data.

87. An apparatus for measuring a sample with a periodic diffracting structure, said apparatus comprising:
   a reflectometer; and
   an ellipsometer, said ellipsometer comprising:
   a source providing a sampling beam of broadband radiation towards the sample, said source comprising an optical fiber;
   a spectrometer detecting simultaneously at a plurality of wavelengths radiation from the sampling beam diffracted by the periodic diffracting structure to provide intensity data;
   a polarizer polarizing said radiation from the source, and an analyzer receiving radiation from the sampling beam diffracted by the periodic diffracting structure to provide an output beam to the spectrometer; and
   a computer deriving from the intensity data a characteristic of the sample related to the structure, said characteristic including at least one of the following: shape of line, line width, period and side wall angle of the structure.

88. The apparatus of claim 87, said sample having a layer associated with the structure, said apparatus further comprising a device causing the polarizer or analyzer to rotate when the sampling beam is directed to the associated layer and not to the diffracting structure, and causing the polarizer and analyzer not to rotate when the sampling beam is directed to the diffracting structure.

89. The apparatus of claim 88, wherein said device causes the polarizer to provide and the analyzer to pass radiation having substantially the same polarization.

90. The apparatus of claim 87, said sample having a layer associated with the structure, further comprising a device causing the polarizer or analyzer to rotate when the sampling beam is directed to the associated layer without the diffracting structure and causing the polarizer or analyzer not to rotate when the sampling beam is directed to the diffracting structure.

91. The apparatus of claim 87, wherein the sampling beam is provided at an oblique angle to a surface of the sample.

92. The apparatus of claim 87, wherein said computer derives a characteristic of the structure from the intensity data.

93. The apparatus of claim 92, wherein the computer derives the characteristic using a database.

94. The apparatus of claim 92, wherein the computer derives shape of lines, linewidth, pitch, height or side wall angle of the structure.

95. The apparatus of claim 92, wherein the computer computes ellipsometric parameters from the intensity data in deriving the characteristic of the structure.

96. The apparatus of claim 87, wherein the spectrometer detects radiation from only a single order diffraction from the periodic diffracting structure.

97. The apparatus of claim 96, wherein the single order diffraction is the zeroth or the first order.

98. The apparatus of claim 87, wherein said source includes an optical fiber.

99. The apparatus of claim 87, said plurality of wavelengths comprising ultraviolet wavelengths.

100. The apparatus of claim 87, wherein said reflectometer and ellipsometer employ common optical elements, said common elements comprising a broadband radiation source, a polarizer and a spectrometer.

101. The apparatus of claim 87, said reflectometer and ellipsometer measuring an optical index and film thickness of the sample.

102. An method for measuring a sample with a periodic diffracting structure, said method comprising:
performing a measurement on the sample by means of a reflectometer and an ellipsometer, said performing comprising:
providing a sampling beam of broadband radiation towards the sample by means of an optical fiber;
detecting simultaneously at a plurality of wavelengths radiation from the sampling beam diffracted by the periodic diffracting structure to provide intensity data;
polarizing said sampling beam before it is provided to the sample, wherein said detecting comprises analyzing radiation from the sampling beam diffracted by the periodic diffracting structure; and
deriving from the intensity data a characteristic of the sample related to the structure, said characteristic including at least one of the following: shape of line, line width, period, height and side wall angle of the structure.

103. The method of claim 102, wherein the sampling beam is provided at an oblique angle to a surface of the sample.

104. The method of claim 102, wherein the deriving derives the characteristic of the sample related to the structure using a database.

105. The method of claim 102, wherein the deriving computes ellipsometric parameters from the intensity data in deriving the characteristic of the sample, related to the structure.

106. The method of claim 102, wherein the detecting detects radiation from only a single order diffraction from the periodic diffracting structure.

107. The method of claim 106, wherein the single order diffraction is the zeroth or the first order.

108. The method of claim 102, said plurality of wavelengths comprising ultraviolet wavelengths.

109. The method of claim 102, further comprising measuring an optical index and film thickness of the sample.

110. The method of claim 102, using the characteristic of the sample in wafer process monitoring, closed-loop control or focus-exposure control in photolithography.

111. The method of claim 102, wherein said polarizing polarizes the broadband radiation so that the sampling beam is in the TE or TM mode, and the detecting detects radiation in the TE or TM mode.

112. The method of claim 102, wherein said sample comprises a plurality of periodic diffracting structures and a substrate comprising one or more layers associated with the structures, wherein said spectroscopic measurements measures film thickness or index of refraction information of said one or more layers only once, and wherein said scatterometric measurements measure each of the structures to obtain data.

* * * * *